(12) United States Patent
DeAnglis et al.

(10) Patent No.: US 10,625,032 B2
(45) Date of Patent: Apr. 21, 2020

(54) SPRAY TIPS FOR SIMULTANEOUS MULTI-DIRECTIONAL DELIVERY OF DISSIMILAR FLUIDS

(71) Applicant: Ethicon, Inc., Somerville, NJ (US)

(72) Inventors: Ashley DeAnglis, Skillman, NJ (US);
Sridevi Dhanaraj, Raritan, NJ (US);
John F. Goodman, Ann Arbor, MI (US)

(73) Assignee: Ethicon, Inc., Somerville, NJ (US)

( * ) Notice: Subject to any disclaimer, the term of this patent is extended or adjusted under 35 U.S.C. 154(b) by 427 days.

(21) Appl. No.: 15/238,105

(22) Filed: Aug. 16, 2016

(65) Prior Publication Data
US 2018/0050163 A1 Feb. 22, 2018

(51) Int. Cl.
*A61M 11/00* (2006.01)
*A61B 17/00* (2006.01)

(52) U.S. Cl.
CPC .......... *A61M 11/007* (2014.02); *A61B 17/00* (2013.01); *A61B 2017/00495* (2013.01); *A61M 2202/04* (2013.01)

(58) Field of Classification Search
CPC .......... A61B 17/00; A61B 2017/00495; A61B 2017/00522; A61B 2017/00504;
(Continued)

(56) References Cited

U.S. PATENT DOCUMENTS

| 5,116,315 A | 5/1992 | Capozzi et al. |
| 5,605,255 A | 2/1997 | Reidel et al. |

(Continued)

FOREIGN PATENT DOCUMENTS

| JP | 2011/067491 | 4/2011 |
| WO | WO 2002/0055138 | 7/2002 |

(Continued)

OTHER PUBLICATIONS

International Search Report re: PCT/US2017/046210 dated Nov. 3, 2017.
Written Opinion re: PCT/US2017/046210 dated Nov. 3, 2017.

*Primary Examiner* — Erich G Herbermann
(74) *Attorney, Agent, or Firm* — David R. Crichton; Leo Kriksunov

(57) ABSTRACT

The present inventions are directed to spray tips for multi-directional or three-dimensional spraying of an unmixed two-part sealant and/or hemostat comprising a first biocompatible component and a biocompatible second component onto a tissue or wound comprising: a hollow body having inside a first component distribution compartment and a second component distribution compartment, said compartments not in fluid communication with each other. The first component can contain one or more biologic components, preferably fibrinogen and the second component can contain one or more biologic component different from the first biologic component, preferably thrombin and/or thrombin precursors. The present inventions are also directed to methods of spraying the unmixed two-part sealant or hemostat using the spray tip and associated components described above by simultaneously expressing the first component and the second component from the syringes.

11 Claims, 17 Drawing Sheets

(58) Field of Classification Search
CPC .... A61B 2017/00513; A61B 2017/005; A61B 2017/00464; A61M 11/007; A61M 2202/04

See application file for complete search history.

(56) References Cited

U.S. PATENT DOCUMENTS

| | | |
|---|---|---|
| 5,605,541 A | 2/1997 | Holm |
| 5,759,169 A | 6/1998 | Marx |
| 6,063,055 A | 5/2000 | Epstein et al. |
| 6,132,396 A | 10/2000 | Antanavich et al. |
| 6,461,325 B1 | 10/2002 | Delmotte et al. |
| 6,863,660 B2 | 3/2005 | Marx |
| 6,877,924 B1 | 4/2005 | Mears et al. |
| 7,776,063 B2 | 8/2010 | Sawhney et al. |
| 8,281,975 B2 | 10/2012 | Criscuolo et al. |
| 8,731,841 B2 | 5/2014 | Boyden et al. |
| 8,888,749 B2 | 11/2014 | Campbell et al. |
| 9,119,606 B2 | 9/2015 | Weadock et al. |
| 9,254,346 B2 | 2/2016 | Pipenhagen et al. |
| 2003/0191496 A1 | 10/2003 | Edwards et al. |
| 2008/0121657 A1 | 5/2008 | Voegele et al. |
| 2008/0317539 A1 | 12/2008 | Brugger |
| 2010/0096481 A1 | 4/2010 | Hull et al. |
| 2011/0147432 A1 | 6/2011 | Heinrich et al. |
| 2011/0264122 A1 | 10/2011 | Bonino et al. |
| 2013/0325059 A1 | 12/2013 | O'Neill |
| 2014/0207186 A1* | 7/2014 | Weadock ........... A61B 17/1155 606/214 |
| 2015/0005698 A1 | 1/2015 | Yokoyama |

FOREIGN PATENT DOCUMENTS

| | | |
|---|---|---|
| WO | WO 2006/0102472 | 9/2006 |
| WO | WO 2014/006738 | 1/2014 |
| WO | WO 2014/0113414 | 7/2014 |

* cited by examiner

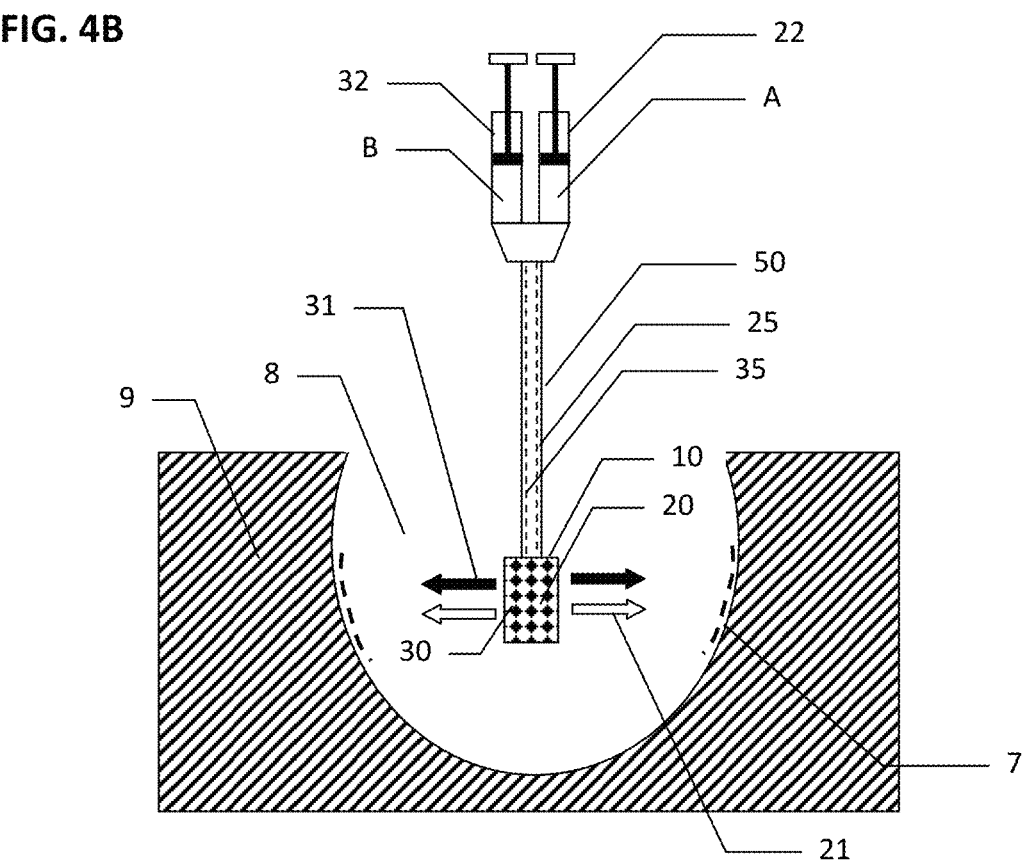

SPRAY TIPS FOR SIMULTANEOUS MULTI-DIRECTIONAL DELIVERY OF DISSIMILAR FLUIDS

The present disclosure relates to spray tip assemblies for use with devices that apply two or more biocompatible, hemostatic, adhesive and/or sealing components without independently of one another while simultaneously spraying the components multi directionally.

BACKGROUND

Drip devices for dispensing two or more biocomponents are known. In the medical device field, such devices are typically used for applying bioadhesives, polymers and other synthetic material used in wound closure. Because of the reactant nature of the biocomponents used to form the bioadhesive, mixing of the components does not occur until the solution is ready to be applied. Mixing of the components too soon before application may result in the premature polymerization reaction or hardening of the mixture, thereby making application of the solution impossible. Thus, in known drip devices, the two or more components are maintained separately until just prior to application. The drip devices may include one or more pre-mixing means for mixing the two or more solutions prior to application. The pre-mixing means may be passive, i.e., spiral configuration in the tubing, or instead may be active, i.e., mixing blade or impeller. Once mixed, the solution may be applied through a needle-like output or may instead be ejected through a spray assembly.

An exemplary device is taught in U.S. Pat. No. 5,116,315, entitled "Biological Syringe System", which discloses a system for delivery two fluids in a mixed composition, comprising a manifold and a discharge assembly. The discharge assembly mixes fluids in a mixing space and then atomizes the mixed fluids in a spray delivered from the assembly. Similarly, the device shown in U.S. Pat. No. 5,605,255, entitled, "Apparatus for Spraying a mixture of Two Components', is an apparatus for spraying a liquid mixture having two syringes, a connecting piece, a premixing chamber, and a reduced volume section downstream from premixing chamber, and an exit aperture for spraying the mixture. The reduced volume section terminates in a homogenization region. U.S. Pat. No. 6,063,055, entitled "Turbulence Mixing Head for a Tissue Sealant Applicator and Spray Head for Same", illustrates a device in which the mixing is performed in a mixing head.

Intermittent use of a biologics spray device, as may be required during a procedure, tends to clog the outlet of the applicator tip. As a result, most applicator assemblies are provided with a number of replacement tips for times when clogging of the tip occurs. Replacing clogged applicator tips interrupts the flow of a procedure, is time consuming and is an added expense. The device in published U.S. Patent Application 2010/0096481, "Self-Cleaning Spray Tip", is described as having the distal end of drip cap assembly with an outlet that changes its configuration—at rest and at a second condition (e.g. during expression). The distal end is described as comprised of a material that permits flexion and expansion. The first and second reactive components are introduced into swirl chambers before mixing and are atomized as ejected through the outlet in a cone-shaped spray.

Persistent air leaks occurring after lung resection procedures are associated with patient discomfort, and increased length and cost of hospitalization. Sealing air leaks has been identified as a significant unmet need, however, there is currently no standard for treatment or prevention. More than 800,000 lung resection procedures are performed globally each year, and the number of procedures is expected to grow in future years as new lung cancer screening guidelines are implemented. Leaks are associated with increased length and cost of hospitalization, patient discomfort and prolonged chest tube management. Rates of persistent air leaks are 15-18% for non-emphysematous patients and up to 50% for patients with emphysema and COPD. The properties of existing sealants also make it difficult to ensure full and continued coverage of the lung, particularly when a minimally invasive technique has been used. Full coverage of the lung is important, because a) leaks can develop at the staple line, adjacent to the staple line, and in the lobes of the lung due to manipulation during the procedure b) the exact location of air leaks in not known. Due to the minimally invasive approach, current sealants must be applied to a deflated lung. Current sealants do not have the physical properties that allow them to maintain coverage of the entire surface of the lung during and after insufflation. Current sealants are applied to the lung in a deflated state and following sealant set, the lung is fully inflated. This results in a several fold change in lung volume, while the sealant in unable to expand to the same degree resulting in sealant crack and loss of seal.

U.S. Pat. No. 5,605,541 titled "Fibrin sealant applicator" discloses a device for applying a fibrin sealant comprising two components which will form said sealant when combined, which device comprises reservoirs for each of said components and a source of gas, wherein each of said reservoirs and said gas in separate fluid communication via a discrete channel to a spray head, said spray head having a first aperture located centrally in an exit end of said spray head through which said gas is discharged, said spray head having a first annular aperture in the exit end of said spray head within first annular aperture is concentric with said first aperture and through which one of said fibrin-sealant-forming components is discharged, and a second annular aperture in the exit end of said spray head being concentric with said first aperture and concentric with, and having a radius larger than said first annular aperture through which the second of said fibrin-sealant-forming components is discharged wherein all of said apertures are in a common plane.

U.S. Pat. No. 5,759,169, titled "Fibrin sealant glue-gun" discloses an applicator for creating a homogeneous film coating of a biological adhesive, the adhesive comprising a first component and a second component, the applicator comprising: (a) a housing having a first dispensing conduit for dispensing said first component and a second dispensing conduit for dispensing said second component; (b) a pressure supply conduit in communication with said dispensing conduits; (c) a first reservoir containing said first component, said first reservoir being in communication with said first dispensing conduit; (d) a second reservoir containing said second component, said second reservoir being in communication with said second dispensing conduit; (e) a first pressure regulator in communication with said first reservoir for controlling pressure supplied through said pressure supply conduit to said first reservoir; and (f) a second pressure regulator in communication with said second reservoir for controlling pressure supplied through said pressure supply conduit to said second reservoir.

U.S. Pat. No. 6,132,396, titled "Apparatus for applying tissue sealant" discloses a manifold for combining first and second components of a material, comprising a body having first and second inlet ports, a tubular dispenser coupled to the body and provided with an outlet and an internal passageway in fluid communication with said outlet, said body having first fluid transport means adapted for transporting said first component from said first inlet port to said internal passageway and second fluid transport means adapted for transporting said second component from said second inlet port to said internal passageway, said first fluid transport means including a hypodermic needle in fluid connection with said first inlet port and having an outlet disposed within said internal passageway, said second fluid transport means including a channel in the body and in fluid connection with said second inlet port and provided with an outlet disposed within said internal passageway the hypodermic needle is located in or able to penetrate the channel whereby said first and second components are directed by said first and second transport means into said tubular dispenser for mixing prior to discharge from the outlet of said tubular dispenser.

U.S. Pat. No. 6,461,325 titled "Fibrin delivery device and method for forming fibrin on a surface" discloses a medical device for delivering volumetric quantities of a first and second biochemically active fluid comprising: a first container adapted to contain the first biochemically reactive fluid and having a first fluid channel; a second container adapted to contain the second biochemically reactive fluid and having a second fluid channel; an atomizer in fluid communication with the first and second channels for separately atomizing the first and second biochemically reactive fluids into an aerosol with at least one energy source of a liquid energy, a mechanical energy, a vibration energy, and an electric energy; a fluid pressurizer for delivering a third fluid under pressure to the first container and the second container to deliver the first fluid and the second fluid under pressure to the atomizer; and a third channel for delivering a catalyst.

U.S. Pat. No. 6,863,660, titled "Fibrin applicator pistol" discloses an applicator for delivering a homogeneous coating of fibrin glue formed from a first component and a second component to a target surface comprising: a first hermetically sealed reservoir containing said first component and having a first inlet conduit in fluid communication with said first component; a second hermetically sealed reservoir containing said second component and having a second inlet conduit in fluid communication with said second component; means for applying positive fluid pressure to said first and second hermetically sealed reservoirs relative to an ambient environment; a first outlet conduit in fluid communication with said first component and terminated by a first atomizer extending into said ambient environment in a first direction and having a first inner diameter; and a second outlet conduit in fluid communication with said second component and terminated by a second atomizer extending into said ambient environment in a second direction intersecting with said first direction and having a second inner diameter; wherein application of fluid pressure to said first and second hermetically sealed reservoirs generates a convergent flow of said first and second component at a fixed ratio of said first component to said second component to form said fibrin glue on said surface.

U.S. Pat. No. 8,731,841, titled "Compositions and methods for therapeutic delivery with frozen particles" discloses a system comprising: at least one computing device; at least one computer program, configured with a computer-readable medium, for use with at least one computer system and wherein the computer program includes a plurality of instructions that when executed on the computing device cause the computing device to direct a pre-determined patterned delivery of a plurality of frozen particle therapeutic compositions to at least one biological tissue of at least one subject by a remote controlled device, the plurality of frozen particle therapeutic compositions including at least two sub-sets of frozen particles that include different therapeutic agents and at least one tracer agent; and compare information related to the delivery with information regarding at least one clinical outcome following receipt by the at least one subject; and at least one imaging device configured to measure the at least one tracer agent and provide real-time feedback control of the plurality of frozen particle therapeutic compositions administered to the at least one subject.

U.S. Patent Application Publication No. 2011/0264122A1 titled "DEVICE FOR APPLYING GLUE ON TISSUES TO BE CONNECTED" discloses a device for applying a connecting glue to the facing extremities of two portions of tissue to be connected through enteric anastomosis performable with a mechanical suturer, the device comprising a diffusing element suppliable with the glue and interposable between the two portions of tissue to be connected, the diffusing element provided with at least two openings for bilateral delivery of the glue towards the two portions of tissue to be connected, wherein said diffusing element is connected in fluid communication to a first sheath, wherein said device is connected to a dispenser of aeriforms under pressure for delivering said aeriform inside the first sheath for nebulising the connecting glue delivered by the diffusing element to the portions of tissue to be connected, and wherein said diffusing element has a deployable structure for cooperating with said mechanical suturer.

U.S. Pat. No. 8,281,975 titled "Surgical apparatus and structure for applying sprayable wound treatment material" discloses a surgical stapling apparatus, comprising: a body portion including a proximal end and a distal end, the body portion supporting an actuating handle member at the proximal end thereof and a staple pusher member at the distal end thereof; an anvil assembly removably mounted at the distal end of the body portion, the anvil assembly is movable toward and away from the body portion; an approximation assembly extending between and operatively connected to the body portion and the anvil assembly, wherein the approximation assembly moves the anvil assembly toward and away from the body portion, the approximation assembly including a shaft configured for releasable connection with the anvil assembly; and a wound treatment material dispersion assembly operatively associated with the approximation assembly, the dispersion assembly including: at least one fluid source, at least one conduit in fluid communication with the at least one fluid source and extending into the shaft of the approximation assembly; and at least one ejection port formed in the shaft of the approximation assembly and is in fluid communication with the at least one conduit wherein the at least one ejection port is configured to dispense fluid from the at least one fluid source to a location between the staple pusher member and the anvil assembly, wherein the approximation assembly includes a nozzle supported on the shaft, wherein the nozzle of the approximation assembly includes a manifold having a plurality of ejection ports, wherein the plurality of ejection ports include: a plurality of first ejection ports for dispensing a first wound treatment material; and a plurality of second ejection ports for dispensing a second wound treatment material different from the first wound treatment material, and wherein the wound treatment dispersion assembly includes a cap operatively connected to the manifold, and wherein the cap defines a channel between an inner surface of the cap and an outer surface of the manifold.

U.S. Pat. No. 9,119,606 titled "Sealant delivery device for anastomotic stapler" discloses a circular anastomosis surgical stapling instrument, comprising: a shaft, an anvil, a stapling head, and a device for applying adhesive components or sealant components to anastomosis site; the device comprising: a hollow housing with a plurality of exit openings and a coupler adapted to mount the device to the shaft of the circular anastomosis surgical stapling instrument; wherein the hollow housing having a top surface and an opposing bottom surface with at least two separate channels within said housing; the plurality of exit openings comprise a plurality of nozzles disposed circumferentially on the to surface and on the bottom surface with the plurality of nozzles in fluid communication with the channels; a manifold connector attached to the hollow housing, the manifold connector is in fluid communication with the channels and adapted to be connected to a dual lumen cannula for supplying the adhesive components or the sealant components; wherein said coupler is adapted to mount the device to the shaft between the anvil and the stapling head of the circular anastomosis surgical stapling instrument; wherein said channels comprise a first channel and a second channel; wherein said nozzles comprise a first set of nozzles in fluid communication with the first channel and a second set of nozzles in fluid communication with the second channel; wherein the hollow housing has a semicircular shape, with a housing gap dividing the hollow housing into two housing arms; and wherein the coupler has a semicircular opening having an inner diameter equal to a diameter of the shaft, and wherein the coupler is adapted to be snapped onto the shaft.

U.S. Patent Application Publication No. 2011/0147432A1 titled "STRUCTURE FOR APPLYING SPRAYABLE WOUND TREATMENT MATERIAL" discloses a wound treatment material dispersion system for use in combination with an anastomotic surgical stapling apparatus, wherein the surgical stapling apparatus includes an anvil assembly supported opposite a staple pusher member, wherein the wound treatment material dispersion system comprises: a disc defining an outer edge and an inner edge, the disc including a plurality of apertures formed therethrough; at least one of an annular inner wall integrally connected to the inner edge of the disc and an annular outer wall integrally connected to the outer edge; and wound treatment material disposed on a surface of the disc.

U.S. Pat. No. 9,254,346 titled "Vascular closure device having a flowable sealing material" discloses a vascular closure device comprising: a hollow, perforated tube; sealing material configured to flow out of the perforated tube and into a tissue tract to close a hole in a blood vessel; a vessel locating member insertable through the perforated tube and the hole, the vessel locating member being axially movable relative to the perforated tube and the hole, the vessel locating member being expandable within the vessel to temporarily seal the hole internally, the vessel locating member comprising a tube having a plurality of slits extending along a length thereof to define a plurality of deformable arms; wherein the vascular closure device is configured to be inserted into the tissue tract; wherein the vascular closure device comprises a plurality of holes so that the sealing material flows out of the vascular closure device into the tissue tract in a direction that is not parallel to the tissue tract, wherein the plurality of holes increase in size moving distally along a length of the vascular closure device to provide dispensing of greater amounts of the sealing material adjacent to the hole in the blood vessel.

U.S. Patent Application Publication No. 2015/0005698 titled "Applicator" discloses an applicator, comprising: a nozzle including an elongated nozzle main body, to which gas and a plurality of kinds of liquids are supplied, and a nozzle head at a distal end of the nozzle main body and configured to jet a mixed solution of the gas and the plurality of kinds of liquids supplied to the nozzle main body, the nozzle main body possessing an outer peripheral surface; a sheath in which the nozzle main body is positioned for relative movement along a longitudinal direction of the nozzle main body, the sheath possessing an inner peripheral surface; the applicator being insertable into a living body to apply the mixed solution to a region in the living body; a gap between the outer peripheral surface of the nozzle main body and the inner peripheral surface of the sheath that is an exhaust path for exhausting gas in the living body to outside of the living body when the pressure in the living body rises; and the sheath including a plurality of side holes at a plurality of positions on the sheath, the plurality of side holes spaced from one another by an equal interval along an axial direction of the sheath, each of the side holes communicating with the gap.

U.S. Pat. No. 8,888,749 titled "Spray for fluent materials" discloses a medical apparatus for applying a biocompatible coating in situ, the apparatus comprising: an elongated barrel having a distal end defining a gas flow outlet; and first and second conduits each having a distal end extending through the gas flow outlet and beyond the distal end of the elongated barrel, the first conduit defining a first exit opening and the second conduit defining a second exit opening, the first and second conduits are configured to deliver a first composition through the first conduit and a second composition through the second conduit, the first and second exit openings are positioned externally of the elongated barrel distally of the gas flow outlet to mix the first composition and the second composition externally of the elongated barrel and the first and second conduits, wherein the distal end of the first conduit has a first beveled tip defining the first exit opening, the first beveled tip defining a first plane having a first axis which is angled with respect to a longitudinal axis of the first conduit and the distal end of the second conduit has a second beveled tip defining the second exit opening, the second beveled tip defining a second plane having a second axis which is angled with respect to a longitudinal axis of the second conduit, the first axis intersecting the second axis at the distal end of the first and second conduits to define an interior angle that is less than about 140 degrees, the first and second beveled tips are oriented to facilitate mixing of the first and second compositions at a location distally of the first and second conduits, wherein the distal end of the first conduit is in direct physical contact with the distal end of the second conduit.

U.S. Pat. No. 7,776,063 titled "In situ materials formation" discloses a method of disposing a crosslinked biocompatible material in a body comprising introducing a solution with an injection system to a fixed position in a body, with the first solution comprising at least one crosslinkable macromer that spontaneously crosslinks in situ to form the crosslinked material, wherein the macromer, within about 1 second of placement at the position, forms the material with sufficient mechanical integrity to remain at the position during the crosslinking process so as to prevent migration of the macromer away from the position.

U.S. Patent Application Publication No. 2013/0325059 titled "Non-Clogging Airless Spray for High Viscosity, High Surface Tension Fluids" discloses a medical device for spraying two liquids comprised of a first and second syringe each syringe having an outlet for a first and second liquid; a connecting piece having first and second channels in communication with said syringe outlets terminating in distal component comprised of a spray cap which contain independent fluid passages for said first and second liquids and a first and second exit surface; wherein first and second exit surfaces of said spray cap contain a plurality of small exit apertures and said first and second exit apertures create a spray pattern which combines and mixes said first and second liquids away from the device.

Patent Publication No. WO2014/006738A1 titled “TREATMENT DEVICE FOR TREATING INSIDE OF ORGANISM LUMEN” discloses a treatment device for treating the inside of an organism lumen is provided with: a long shaft inserted into a blood vessel; a support section having a proximal end side which is supported by the shaft and also having a distal end side which is capable of expanding and contracting in the direction perpendicular to the axial direction of the shaft; and a deformable application section provided on the distal end side of the support section . The deformable application section is brought into contact with the wall of the blood vessel by the expansion of the distal end side of the support section and has a discharge opening which, when the deformable application section is in contact with the wall of the blood vessel, is located near the wall and can discharge a substance to be applied.

Japanese Patent Publication No. JP2011/067491A titled “FLUID JET DEVICE” discloses as an unmet need to effectively penetrate a blood clot and the like with a pulsation flow while removing the whole of blood clot and the like by emitting a jet of a fluid widely, and discloses a solution as being an auxiliary jet orifice that is opened to a direction different from a direction of a jet orifice emitting a pulsation flow, and it is connected to an auxiliary fluid path which is different from a connection fluid path connected to the jet orifice. The fluid is continuously emitted from the auxiliary jet orifice by continuously sending the fluid to the auxiliary fluid path. The result is that the pressure of pulsation flow does not decrease because of the auxiliary jet orifice, and the cutting performance of the pulsation flow is kept while the fluid can be emitted from the auxiliary jet orifice within the area where the pulsation flow cannot be emitted. Then, the auxiliary jet orifice can keep the cutting performance by continuously emitting the jet of the fluid even when the pressure of the fluid disperses and decreases by emitting the jet of the fluid widely. As a result, the blood clot and the like can be penetrated effectively by the pulsation flow while the whole of blood clot and the like can be removed by emitting the jet of the fluid widely.

SUMMARY

Briefly, the present inventions are directed to spray tips for multidirectional or three-dimensional spraying of an unmixed two-part sealant and/or hemostat comprising a first biocompatible component and a biocompatible second component onto a tissue or wound comprising: a hollow body having inside a first component distribution compartment and a second component distribution compartment, said compartments not in fluid communication with each other; conduits to supply the first component into the first component distribution compartment and the second component into the second component distribution compartment; and a plurality of first exit orifices on spray tip in fluid communication with the first component distribution compartment and a plurality of second exit orifices on spray tip in fluid communication with the second component distribution compartment. The first exit orifices are positioned alternatingly with said second exit orifices around the spray tip and point towards outside of the spray tip in multiple directions. The spray tip can be further attached through a cannula to component expression pumps containing the first component and second component. The component expression pumps comprise syringes that are conventionally associated with dual syringe devices. The spray tip can further contain a plurality of channels in fluid communication with the component distribution compartments and the exit orifices, and wherein said channels are positioned between said component distribution compartments and the exit orifices. The first component can contain one or more biologic components, preferably fibrinogen and the second component can contain one or more biologic component different from the first biologic component, preferably thrombin and/or thrombin precursors.

The exit orifices can be directed towards an area encompassing a solid angle Ω between 2π and 4π steradian. Alternatively, the exit orifices can be directed towards an area encompassing approximately a sphere or approximately a hemisphere, still further an area encompassing a solid angle Ω equal to about 2π steradian or an area encompassing approximately a cylinder formed circumferentially around the spray tip.

The present inventions are also directed to methods of spraying the unmixed two-part sealant or hemostat using the spray tip and associated components described above by simultaneously expressing the first component and the second component from the syringes into the cannula; allowing the first component to enter the first component distribution compartment and the second component to enter the second component distribution compartment inside the spray tip without mixing; and simultaneously spraying the first component through the first exit orifices and the second component through the second exit orifices in multiple directions around the spray tip. In accordance with this method, the spray can be performed over a solid angle Ω between 2π and 4π steradian. The methods can further comprise the steps of inserting the spray tip into a body cavity or a wound cavity prior to expressing the components; and allowing the first component and the second component intermix in the body cavity or the wound cavity.

BRIEF DESCRIPTION OF THE DRAWINGS

FIG. 1 illustrates directions of spray according to an embodiment of the present invention.

FIG. 2 illustrates directions of spray according to an embodiment of the present invention.

FIG. 3 illustrates directions of spray according to an embodiment of the present invention.

FIGS. 4*a* and 4*b* show schematic representations of embodiments of the present invention.

FIG. 5 shows a schematic cross-sectional representation of an embodiment of the present invention.

FIG. 6 shows a schematic cross-sectional representation of an embodiment of the present invention.

FIG. 7 shows a schematic perspective representation of an embodiment of the present invention.

FIG. 8 shows a schematic perspective cutout representation of an embodiment of the present invention.

FIG. 9 shows a schematic perspective cutout representation of an embodiment of the present invention.

FIG. 10 shows a schematic perspective representation of an embodiment of the present invention.

FIG. 11 shows a schematic exploded view representation of an embodiment of the present invention.

DETAILED DESCRIPTION

Briefly, the present invention relates to a spray tip (spray head) for multidirectional, preferably at least three-dimensional spraying of a two-part adhesive, sealant and/or hemostat (such as fibrin glue comprising fibrinogen and thrombin) onto a tissue or wound without prior mixing of the two-part composition within the spray tip, comprising: a hollow body having inside a first component distribution compartment and a second component distribution compartment, said compartments not in fluid communication with each other; at least two conduits to supply the first component into the first component distribution compartment and the second component into the second component distribution compartment; a plurality of exit orifices directing flow of each part of the two-part sealant towards outside of the spray tip in more than one direction, without mixing. The first exit orifices are positioned alternatingly with second exit orifices around the spray tip and point towards the outside of the spray tip in multiple directions. Preferably there is no mixing of the two-part composition within the spray tip as the mixing can occur on the surfaces onto which the two part composition is sprayed. In this embodiment, some mixing can occur in flight between the spray tip exits and surface of the tissue.

Figure 1:
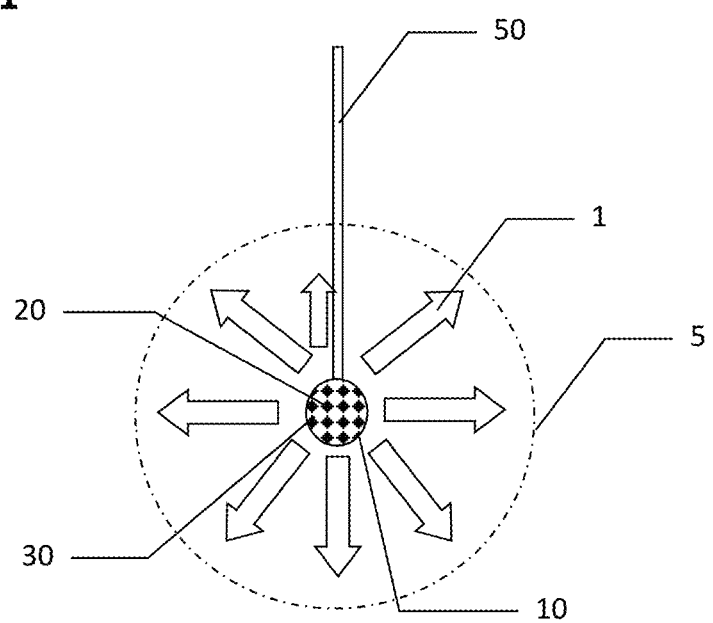

In embodiments of the present invention, the spray is performed multi-directionally at the same time, such as circumferentially around the spray tip, such as in 360 degrees around the spray tip. In some embodiments of the present invention, and referring to FIG. 1, the spray is performed multi-directionally at the same time, with the spray direction schematically indicated by arrows 1 targeting or encompassing substantially a surface of a whole imaginary sphere 5 surrounding the spray tip 10. As schematically shown in FIG. 1, spray tip 10 has a plurality of exit nozzles or exit orifices 20, 30 through which components A and B of the two-part composition are expelled without mixing. Components A and B are supplied via cannula 50 through individual conduits.

According to the embodiment shown in FIG. 1, spray is performed over a solid angle Ω substantially equal or close to 4π steradian, such as Ω equal from about 3.8 to 4π steradian.

Figure 2:
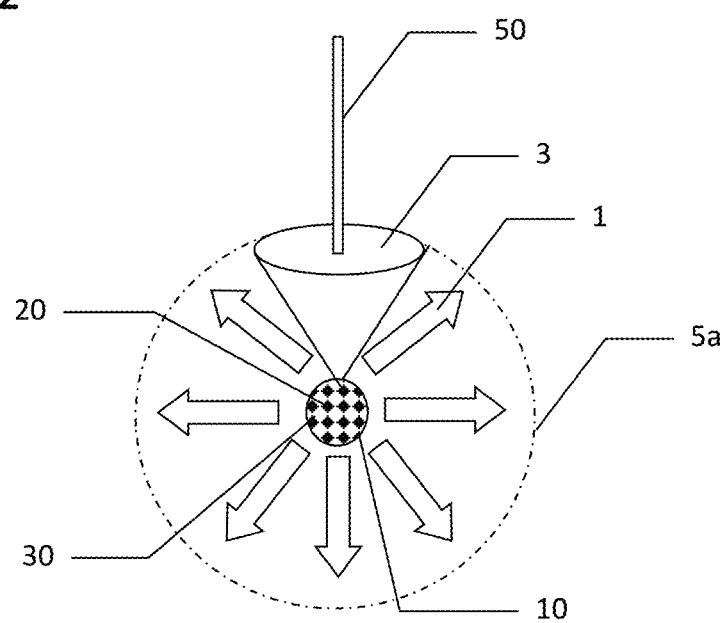

As shown in FIG. 2, in some embodiments, spray is performed towards a surface of a partial imaginary sphere 5a surrounding the spray tip 10, with no spray in the area of cone 3 which surrounds cannula 50 and expands from spray tip 20 towards imaginary sphere 5a. According to the embodiment shown in FIG. 2, spray is performed over a solid angle Ω corresponding to a partial sphere but larger than a half sphere, i.e. 2π<Ω<4π, such as with solid angle Ω equal to 2.5π, 3π, 3.5π, 3.75π steradian.

Figure 3:
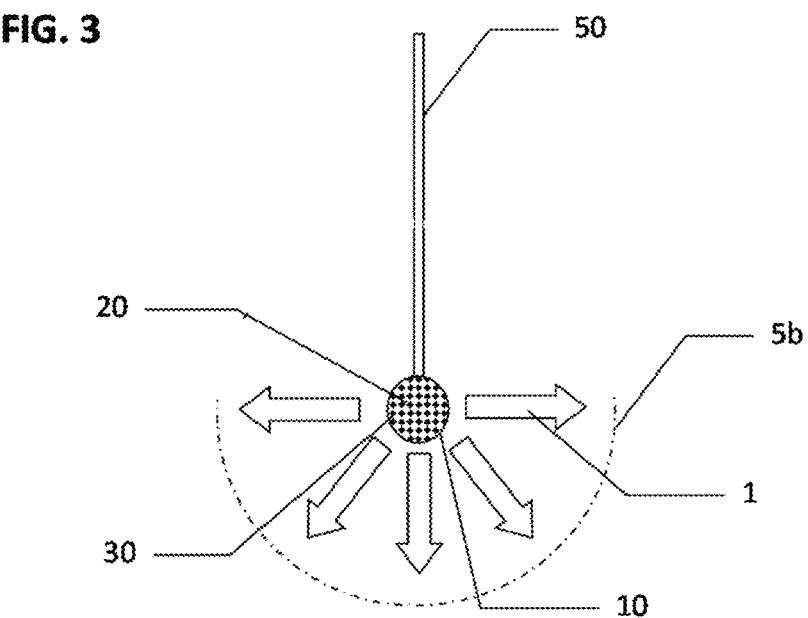

As shown in FIG. 3, in some embodiments, spray is performed towards a surface of a partial imaginary half-sphere 5b surrounding the spray tip 10 and opposite cannula 50, with no spray in the area of half-sphere (not shown) which surrounds cannula 50. According to the embodiment shown in FIG. 3, spray is performed over a solid angle Ω corresponding to about half sphere such as with solid angle Ω equal to 2π steradian.

Figure 4A:
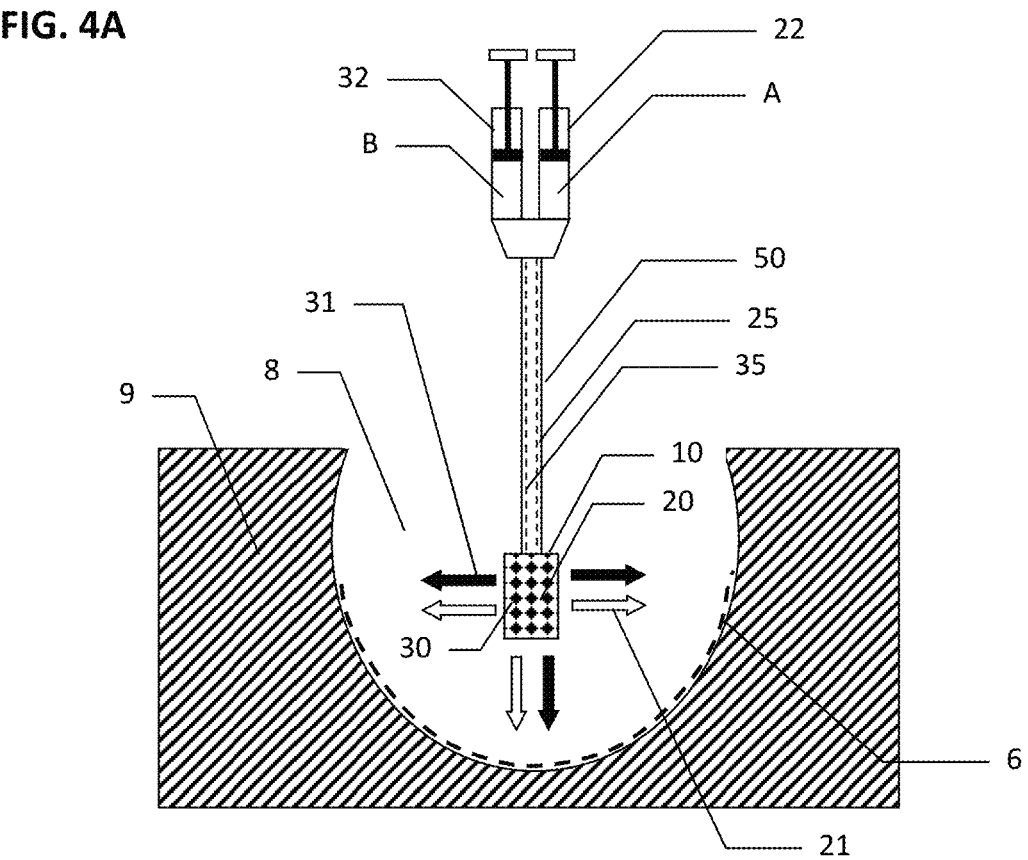

Referring now to FIG. 4a, a schematic representation of an embodiment of the present invention is shown, with spray tip 10 attached to cannula 50 containing two conduits 25 and 35 for conducting components A and B, respectively. Opposite spray tip 10, component expression pumps such as syringes 22 and 32 contain components A and B, respectively. Syringes 22 and 32 are connected directly to conduits 25, 35 for conducting components A and B, respectively to spray nozzle 10 without mixing. Spray tip 10 and part of cannula 50 are shown inside body 9 cavity 8. Upon expressing components A and B from syringes 22 and 32, components A and B travel through conduits 25, 35 into spray tip 10 and are sprayed, separately, from a plurality of orifices 20, 30 forming spray streams 21, 31 of components A and B, respectively. Components A and B are then deposited towards the sides of the spray tip 10 and towards the direction opposite cannula 50 connection to the spray tip 10 onto a surface defined by approximately hemispherical solid angle and shown schematically as dashed line 6. Components A and B, as they are deposited onto tissue surface in the area 6, intermingle and react, resulting in forming of a tissue sealant or hemostat or both. Orifices 20, 30 are positioned on spray tip 10 so as to facilitate uniform distribution of components A and B, in alternating design, for instance in an interdigitated format, checkers format, or similar intermixed format. In one embodiment, one orifice 20 is proximate to next orifice 30, which in turn is proximate to next orifice 20 and so on. In one embodiment, each orifice 20 is at least partially surrounded by several orifices 30, while each orifice 30 is at least partially surrounded by several orifices 20. In another embodiment, a cluster of orifices 20 is next to a cluster of orifices 30 which is in turn proximate to next cluster of orifices 20 and so on.

Referring now to FIG. 4b, a schematic representation of an embodiment of the present invention similar to the embodiment of FIG. 4a is shown. In this embodiment, components A and B are deposited towards the sides of the spray tip 10 and circumferentially around spray tip 10, but not towards the direction opposite cannula 50 connection to the spray tip 10, with resulting spray onto a surface defined by approximately cylindrical shape and shown schematically as dashed line 7.

Figure 5:
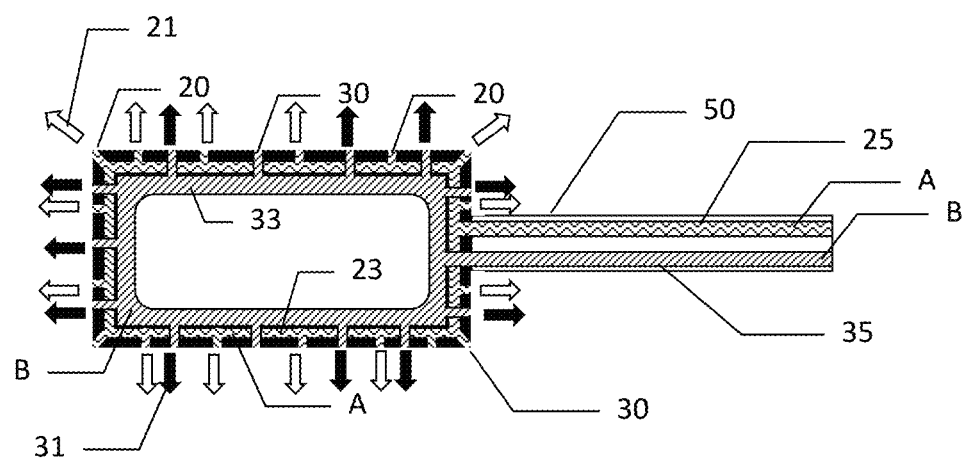

Referring now to FIG. 5, a schematic representation of an embodiment of the present invention is shown, with spray tip 10 attached to cannula 50 containing two conduits 25, 35, for conducting components A and B, respectively. Spray tip 10 comprises a hollow body with two separate compartments inside, component A distribution compartment 23 and component B distribution compartment 33. Component A distribution compartment 23 is in fluid communication with conduit 25 and with all orifices 20. Component B distribution compartment 33 is in fluid communication with conduit 35 and with all orifices 30. As shown, components A and B travel through conduits 25, 35 into spray tip 10 and enter respectively component A distribution compartment 23 and component B distribution compartment 33, after which components A and B are sprayed, separately, from respectively plurality of orifices 20, 30 forming spray streams 21, 31 of components A and B respectively. Only several sprays streams 21, 31 are schematically shown by respectively light and dark arrows in FIG. 5, but it is understood that every exit orifice 20, 30 will generate spray streams 21, 31. As shown in FIG. 5, the spray is performed in all directions encompassing a sphere, i.e. over a solid angle 4π. As shown, orifices 20, 30 are positioned on spray tip 10 in alternating design or intermingled, with one type following another so as to facilitate uniform distribution of components A and B. Such alternating, interlaced, or interspersed positioning of both types of orifices 20, 30 facilitates a good mixing of components A and B when they are deposited on to tissue or wound surface.

Figure 6:
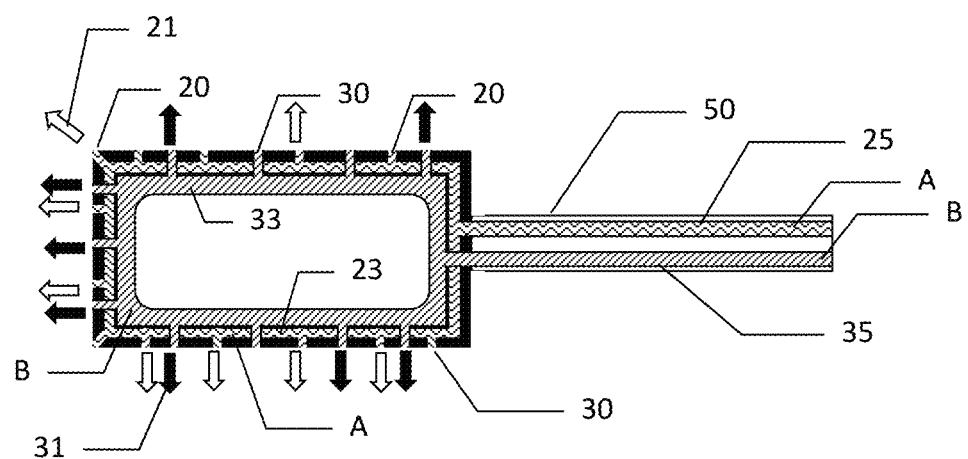

Referring now to FIG. 6, in another embodiment, spraying is performed only over about a half-sphere opposite cannula 50, with no spray performed in the direction of cannula 50.

Figure 7:
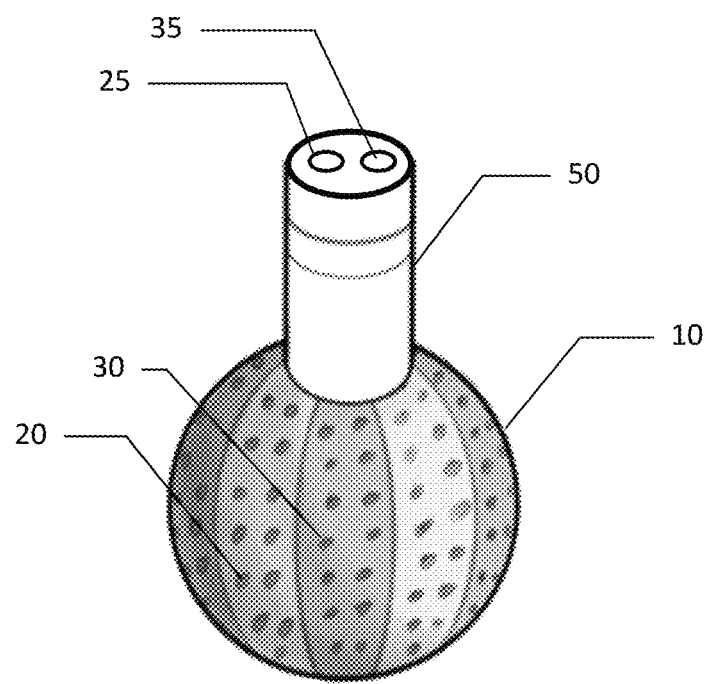

Referring now to FIG. 7, in one embodiment, spray tip 10 has substantially a spherical shape, with arrays of exit orifices 20, 30 arranged in alternating longitudinal zones.

Figure 8:
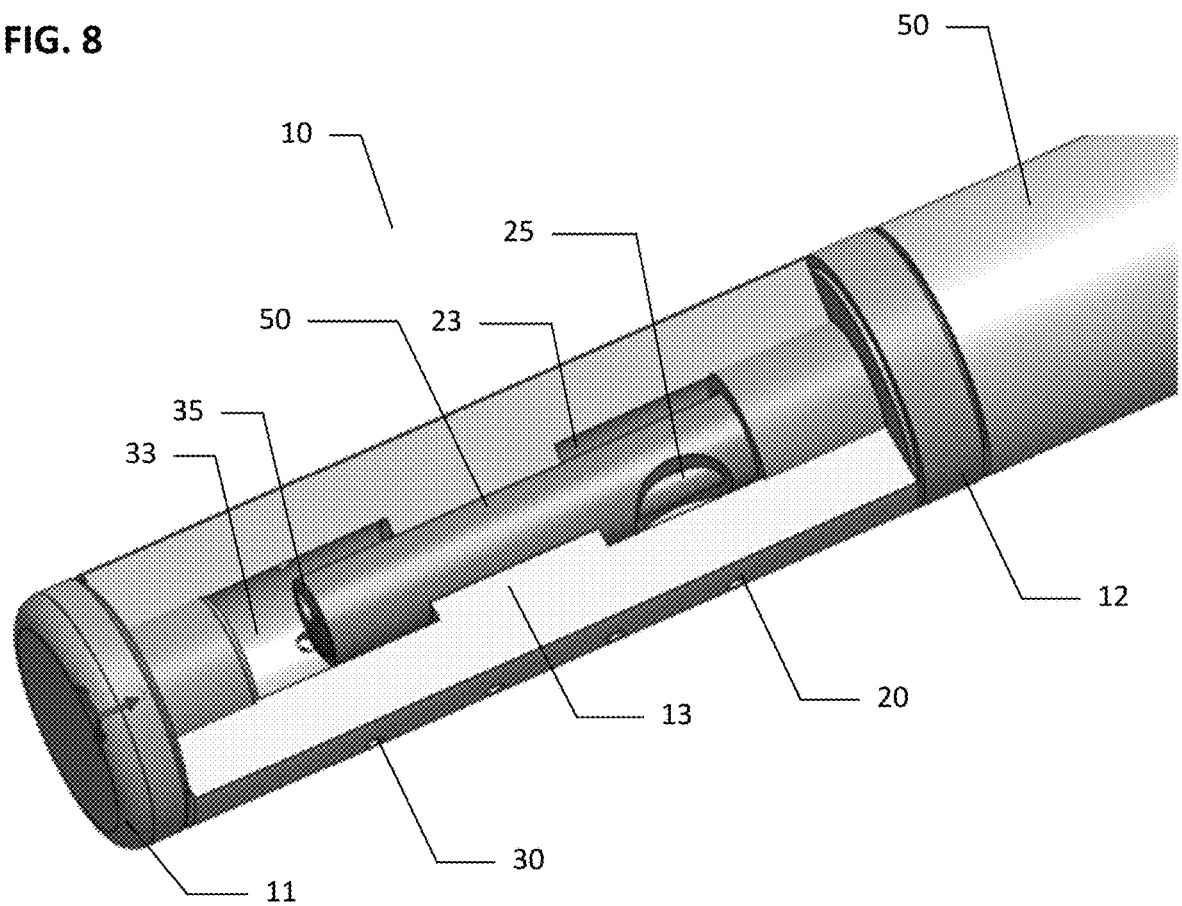
Figure 9:
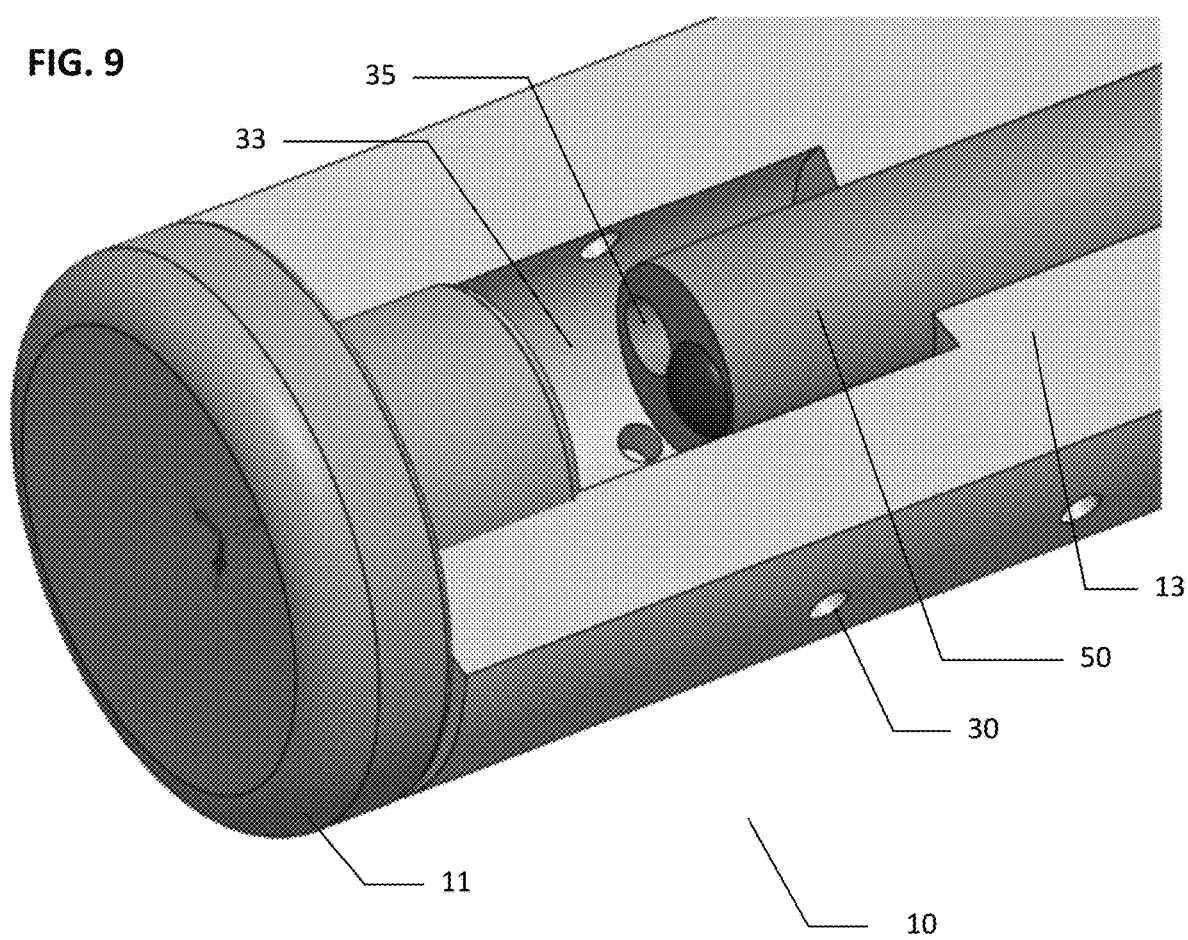
Figure 10:
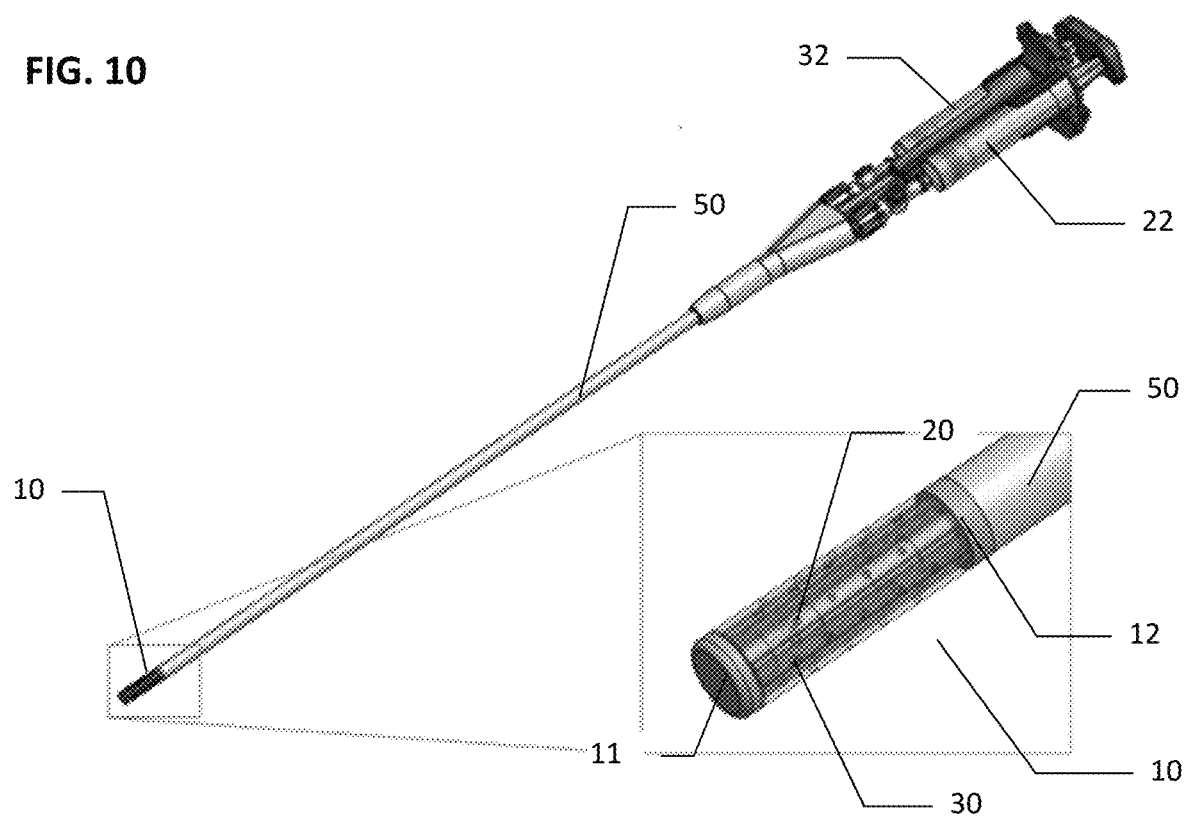
Figure 11:
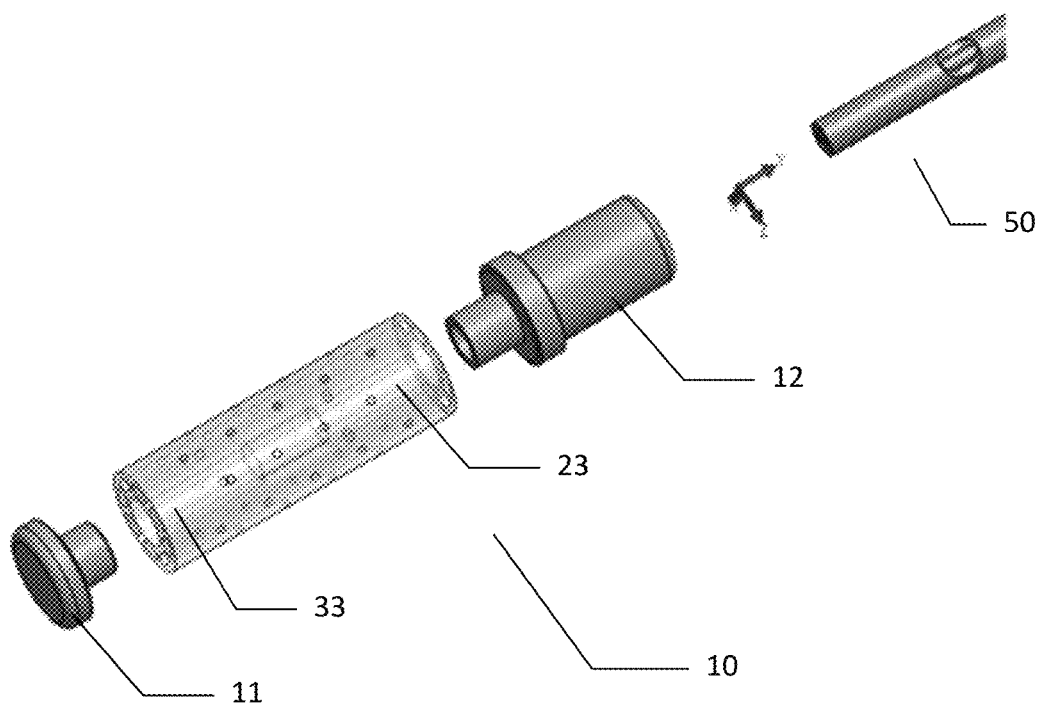
Figure 12:
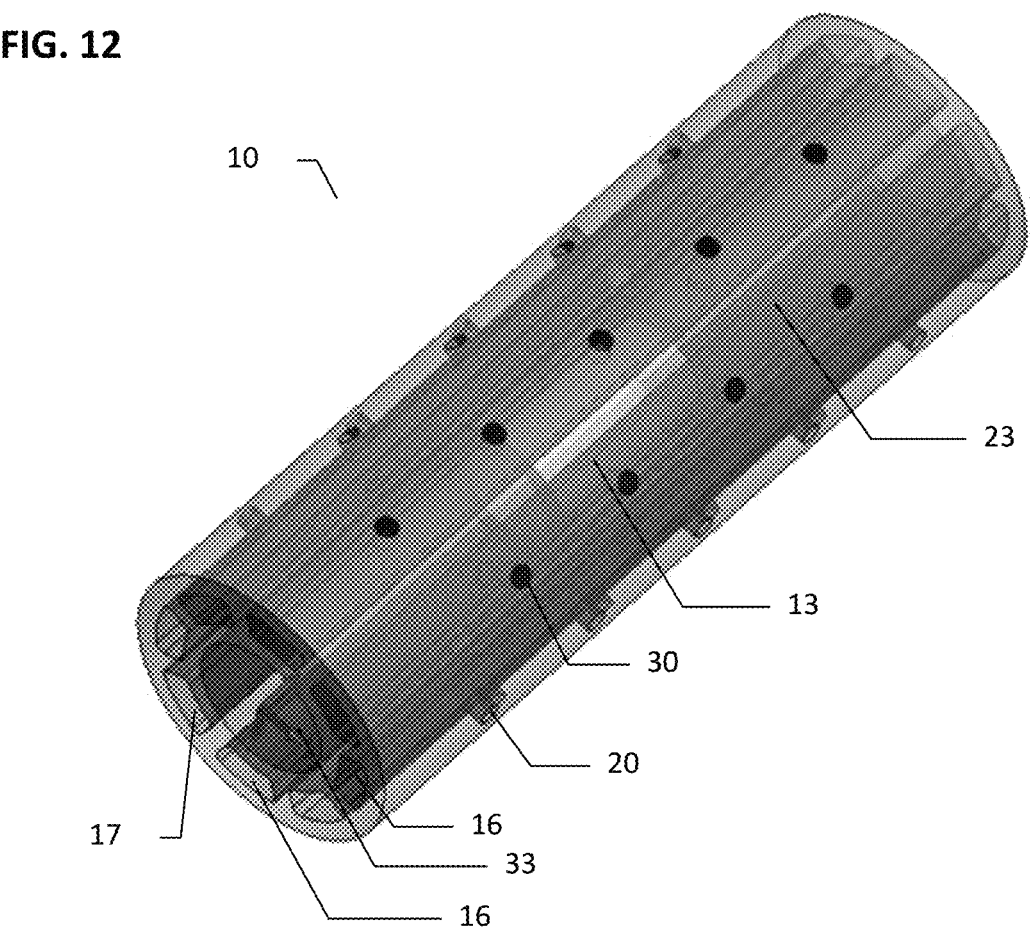
FIG. 12 shows a schematic semi-transparent perspective representation of an embodiment of the present invention.
Figure 13:
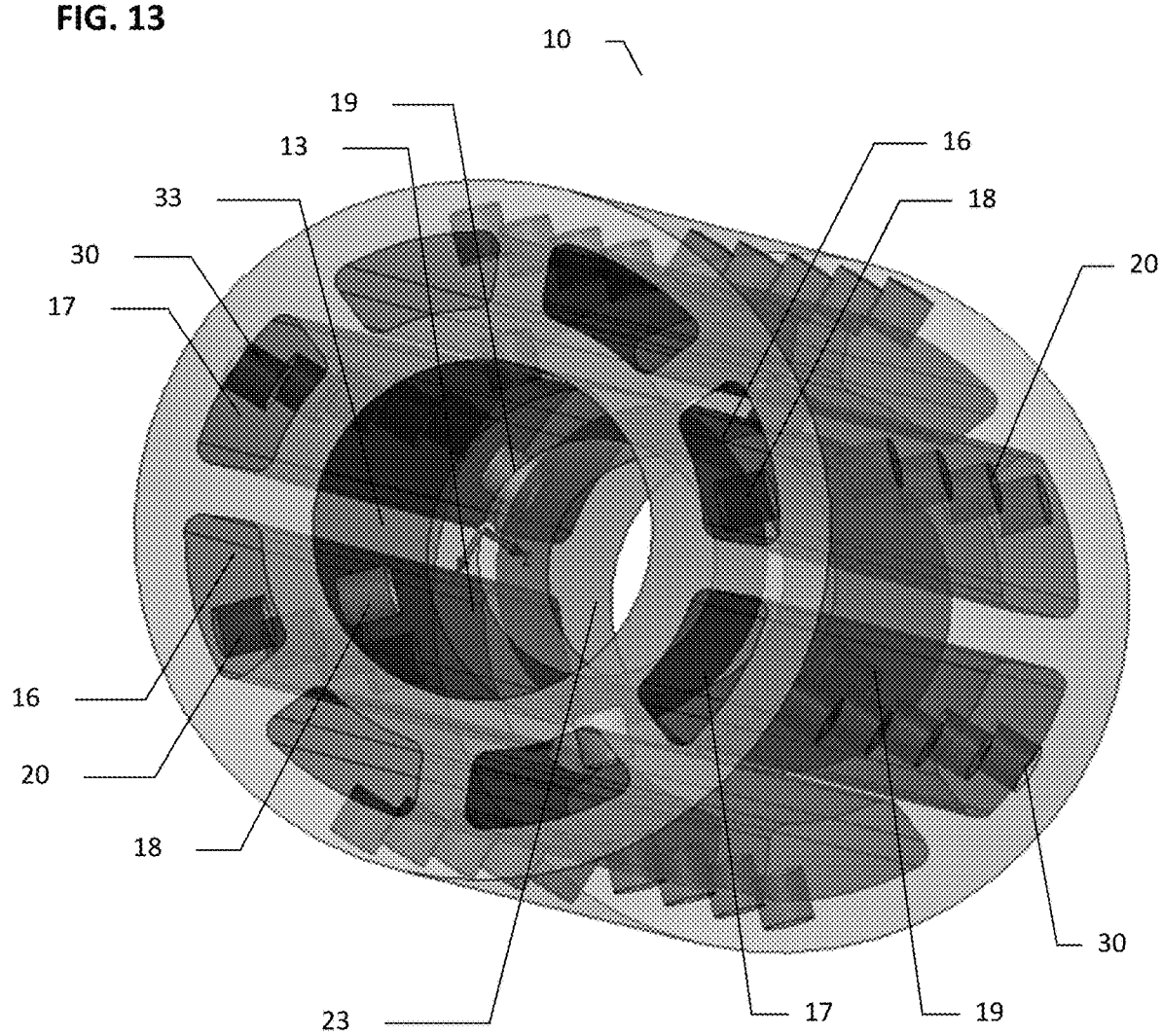
FIG. 13 shows a schematic semi-transparent perspective representation of an embodiment of the present invention.

Referring now to FIGS. 8 and 9, an alternative embodiment of the present invention is shown, with spray tip 10 having a generally hollow cylindrical shape attached to cannula 50 via adapter 12. As shown, spray tip 10 comprises a hollow body with two separate compartments inside, component A distribution compartment 23 and component B distribution compartment 33 separated by separator 13. Spray tip 10 is capped at the end opposite adapter 12 by endcap 11. Component A distribution compartment 23 is in fluid communication with conduit 25 and with all orifices 20. Component B distribution compartment 33 is in fluid communication with conduit 35 and with all orifices 30. As shown, components A and B travel through conduits 25, 35 into spray tip 10 and enter respectively component A distribution compartment 23 and component B distribution compartment 33, after which components A and B are sprayed, separately, from respectively plurality of orifices 20, 30. In this embodiment, all component A spraying orifices 20 are located around component A distribution compartment 23 in the portion of the spray tip 10 proximal to adapter 12, while all component B spraying orifices 30 are located around component B distribution compartment 33 in the portion of the spray tip 10 proximal to endcap 11. No mixing of components A and B is performed inside spray tip 10.

Referring now to FIGS. 10-13, an embodiment of the present invention similar to the embodiment of FIGS. 8-9 is shown, with spray tip 10 having a generally hollow cylindrical shape attached to cannula 50 via adapter 12. As shown, spray tip 10 comprises a hollow body with two separate compartments inside, component A distribution compartment 23 and component B distribution compartment 33 separated by separator 13. Spray tip 10 is capped at the end opposite adapter 12 by endcap 11. Component A distribution compartment 23 is in fluid communication with conduit 25 and component B distribution compartment 33 is in fluid communication with conduit 35.

A plurality of axial channels 16 and 17 run axially along the spray tip 10 cylindrical body, and are positioned one after another around the circumference of the spray tip 10. Axial channels 16 are in fluid communication with component A distribution compartment 23 through vias or openings 18, and are also in fluid communication with all orifices 20. Axial channels 17 are in fluid communication with component B distribution compartment 33 through vias 19, and are also in fluid communication with all orifices 30.

In the embodiments shown in FIGS. 10-13, Components A and B travel through conduits 25, 35 (not shown in FIGS. 10-13) into spray tip 10 and enter respectively component A distribution compartment 23 and component B distribution compartment 33, after which components A and B are passing through correspondingly vias 18 and 19 into axial channels 16 and 17 and are sprayed, separately, from respectively plurality of orifices 20, 30. In this embodiment, all component A spraying orifices 20 are in several axial arrays arranged along the whole or most of the length of spray tip 10. Similarly, all component B spraying orifices 30 are in several axial arrays arranged along the whole or most of the length of spray tip 10. Arrays of orifices 20 are interlaced (or arranged one after another in alternating design) with arrays of orifices 30 so that around the circumference of the cylindrical spray tip 10 array of orifices 20 is followed by array of orifices 30, followed again by array of orifices 20. No mixing of components A and B is performed inside spray tip 10.

Figures 14A, 14B:
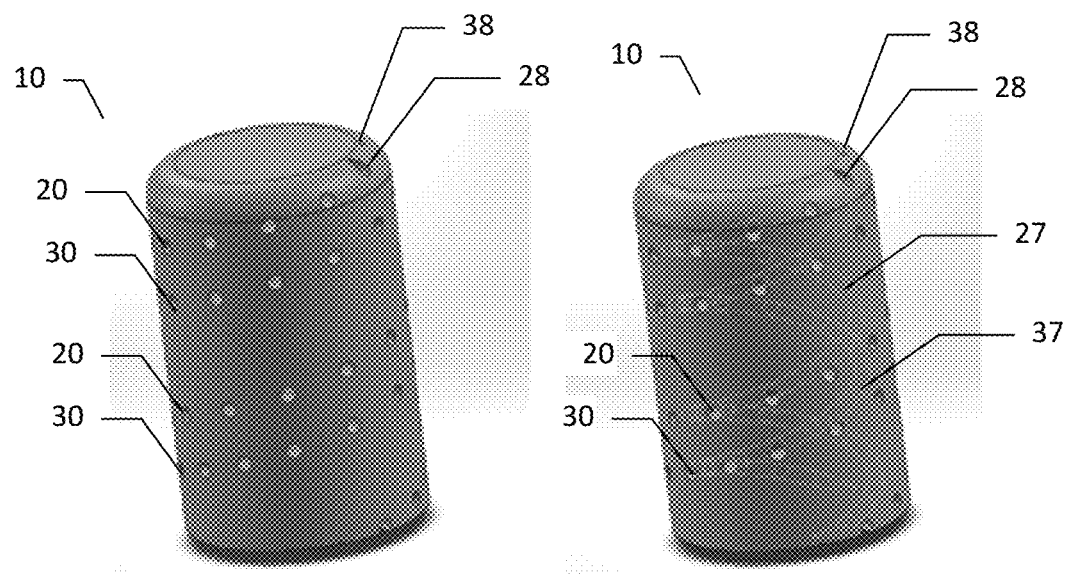
FIGS. 14a and 14b show schematic perspective representation of embodiments of the present invention.

Referring now to FIG. 14, an alternative embodiment of the present invention is schematically shown, with spray tip 10 having two internal generally helical channels 27 and 37 which are fed components A and B from conduits 25 and 35 respectively, resulting in exit orifices 20 and 30 positioned around the spray tip 10 and enabling spraying in directions orthogonal to the spray tip 10 cylindrical surface. Channels 27 and 37 correspond to component A distribution compartment 23 and component B distribution compartment 33 respectively. Optional additional exit orifices 28 and 38 are located on the base of cylindrical tip 10 for spraying also in the axial direction, thus providing a semispherical spray pattern. No mixing of components A and B is performed inside spray tip 10.

Figure 15:
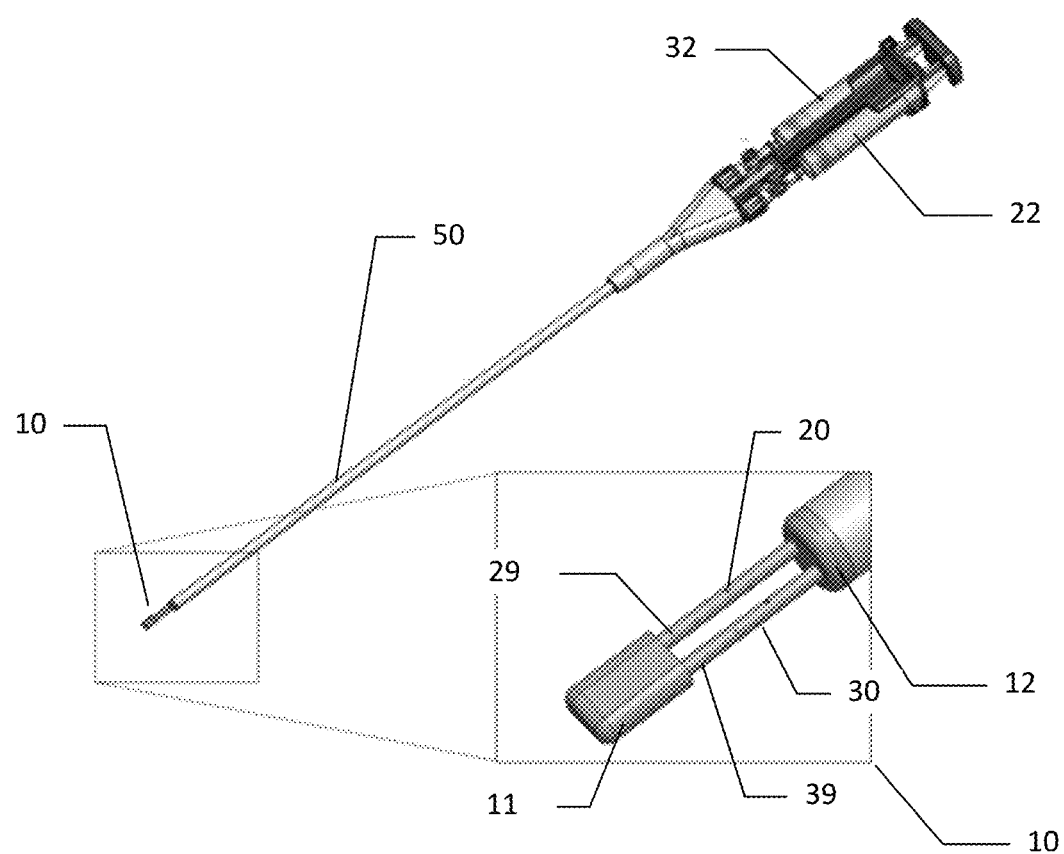
FIG. 15 shows a schematic perspective representation of an embodiment of the present invention.
Figure 16:
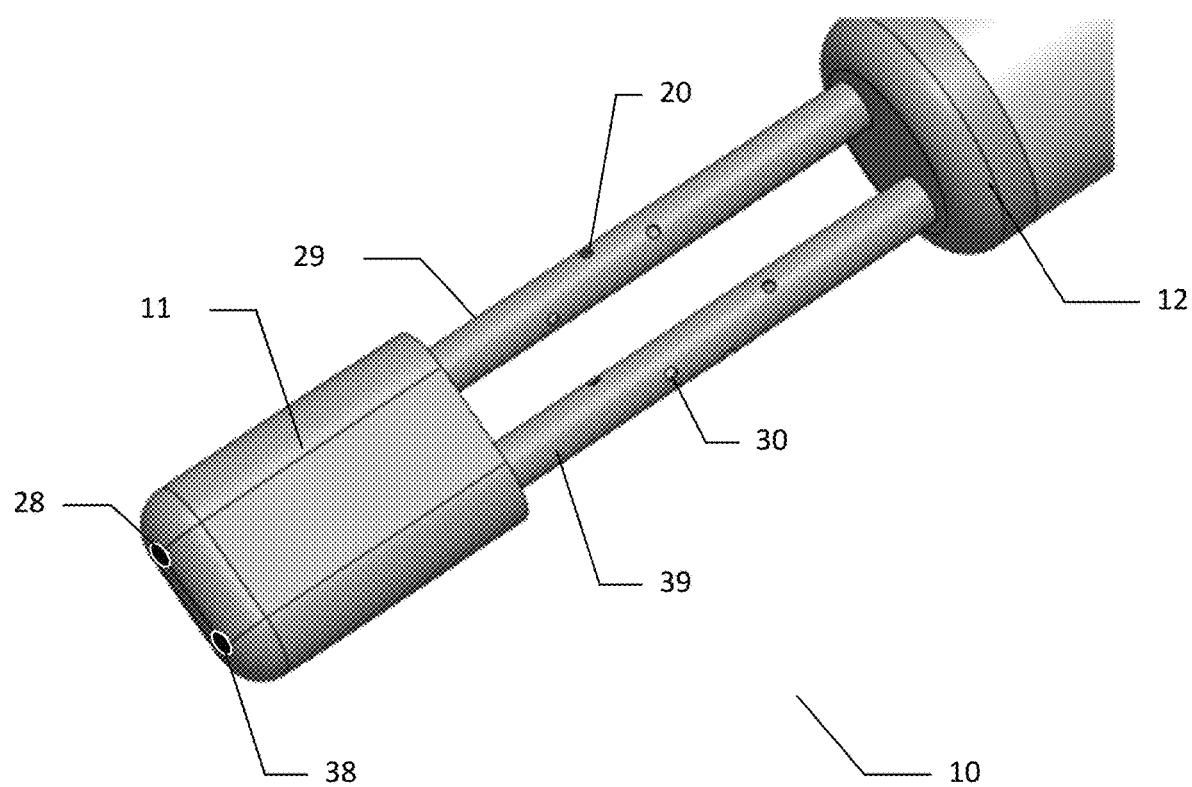
FIG. 16 shows a schematic perspective representation of an embodiment of the present invention.

Referring now to FIGS. 15 and 16, an alternative embodiment of the present invention is shown, with spray tip 10 formed by two tubes 29 and 39 positioned in parallel and side by side between adapter 12 and endcap 11, with a gap between tubes 29 and 39 ranging from about 1 mm to about 15 mm, such as 3, 5, 7, 10 mm. Adapter 12 connects tip 10 to cannula 50. Exit orifices 20 are openings or apertures formed in tube 29 along its length and around its circumference. Exit orifices 30 are openings or apertures formed in tube 39 along its length and around its circumference. As shown, components A and B travel from cannula 50 into closed-end tubes 29 and 39. Components A and B are sprayed, separately, from respectively plurality of orifices 20, 30. Tubes 29 and 39 correspond to component A distribution compartment 23 and component B distribution compartment 33 respectively. No exit orifices 20, 30 are formed in tubes 29, 39 facing the opposite tube to prevent spraying component A onto component B exit orifices and vice versa. There are optional additional exit orifices 28 and 38 located on the endcap 11 for spraying also in the axial direction, thus providing a semispherical spray pattern. In this optional version, tubes 29 and 39 are not closed-end tubes. No mixing of components A and B is performed inside spray tip 10.

According to embodiments of the present invention, a multi-directional or multi-dimensional or three dimensional spray tip or spray head is described for delivery of a liquid sealant, including single part sealant, more preferably multi-part sealant, such as a two-part sealant or hemostat or both, such as liquid fibrin sealant comprising solutions of fibrinogen and thrombin, capable of dispensing a fine spray or mist onto the lung, pleura and chest wall simultaneously in several directions. Upon full inflation of the lung, the thin layer of sealant coated on the surface of the lung would contact the sealant coated on the chest wall to adhere the surfaces while minimizing the sealant needed to achieve such adherence and to seal air leaks. In addition to fibrin sealants, this concept of three dimensional spraying or misting would also be applicable to other protein-based sealants or synthetic sealants, or protein/synthetic combinations sealants and hemostats.

Simultaneous multidirectional spraying allows coating of tissue surfaces on a single pass delivery of sealant. Using unidirectional forward spraying, both pleura surfaces can't be coated simultaneously, and requires additional time and multiple passes to coat all surfaces uniformly. No pressurized gas (e.g. air, CO2, etc.) is required for spraying of the sealant. The delivery can be achieved by manual delivery and application of the liquid components using a double barrel syringe system, or modification thereof. The use of an air-less or gas-less spray delivery system of the biologics improves the safety and ease of use of the system.

Advantageously, the present invention is not associated with clogging of the spray tip since the components are always kept separated within the device and spray tip/spray head. No changing of clogged tips will be required. Clogging can occur with some fibrin sealant delivery devices since mixing occurs within the tip. Changing of tips extends the procedural time and interrupts the surgeon's rhythm.

Advantageously, the two liquid components of the present invention react on the tissue surface upon contact. Adhesion between the lung and chest wall is created when the two liquid components react on the tissue surface. This reaction reduces/eliminates the criticality of the timing between application of the sealant and expansion of the lung.

Advantageously, the spraying and misting action can deliver the sealant in all directions from the spray tip, nearly 360° rather than the traditional cone-shaped pattern of most spray tips. The sealant could be delivered as a burst which could simultaneously coat the surfaces within the thoracic cavity to a deflated or partially deflated lung. The spray head could be used in open procedures or during endoscopic/VATS (video-assisted thoracoscopic surgery) procedures.

Advantageously, the spray tip is designed to maintain isolation of the components A and B until after they leave the device and prevents clogging of the device during interrupted application.

Viewed from the end, the resulting spray pattern from the device is a circular array of streams projecting radially from the spray head. The streams are comprised of alternating biologics. When the streams hit the walls of the body cavity of the patient, they disperse and comingle, allowing them to polymerize into the desired sealing structure.

The internal diameter of conduits 25, 35 is from about 0.5 mm to about 5 mm, more preferably 1 to 3 mm, such as 1, 1.5, 2, 3 mm. The diameter of exit orifices 20, 30 is from about 0.1 mm to about 2 mm, more preferably 0.2 mm to 1 mm, such as 0.25, 0.5 0.75 mm. In one embodiment, exit orifices 20, 30 are drilled perpendicular to the surface if the spay head 10, resulting in spray is perpendicular to the spray head 10 surface. In an alternative embodiment, at least some exit orifices 20, 30 are drilled under angle and not perpendicular to the surface if the spay head 10, resulting in some spray directions is not perpendicular to the spray head 10 surface.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

We claim:

1. A spray tip for multidirectional or three-dimensional spraying of an unmixed two-part sealant and/or hemostat comprising a first biocompatible component and a biocompatible second component onto a tissue or wound comprising: a hollow body having inside a first component distribution compartment and a second component distribution compartment, said first and second component distribution compartments not in fluid communication with each other; conduits to supply the first biocompatible component into the first component distribution compartment and the second biocompatible component into the second component distribution compartment; a plurality of first exit orifices on spray tip in fluid communication with the first component distribution compartment and a plurality of second exit orifices on spray tip in fluid communication with the second component distribution compartment; wherein said plurality of first exit orifices are positioned alternatingly with said plurality of second exit orifices around the spray tip; wherein said spray tip has a generally cylindrical shape, wherein said plurality of first and said plurality of second exit orifices point towards outside of the spray tip towards an area encompassing approximately a cylinder formed circumferentially around the spray tip, wherein said plurality of first exit orifices and said plurality of second exit orifices deliver a spray pattern of said first biocompatible component and said second biocompatible component in a circular array that projects radially from the spray tip and orthogonally to a cylindrical surface of said spray tip.

2. The spray tip of claim 1, wherein said spray tip is further attached through a cannula to component expression pumps containing the first biocompatible component and second biocompatible component.

3. The spray tip of claim 2, wherein said component expression pumps comprise syringes.

4. A method of spraying the unmixed two-part sealant or hemostat using the spray tip of claim 3, comprising the steps of: a) Simultaneously expressing the first biocompatible component and the second biocompatible component from the syringes into the cannula; b) Allowing the first biocompatible component to enter the first component distribution compartment and the second biocompatible component to enter the second component distribution compartment inside the spray tip without mixing; c) Simultaneously spraying the first biocompatible component through the plurality of first exit orifices and the second biocompatible component through the plurality second exit orifices in multiple directions around the spray tip.

5. The method of claim 4, further comprising the steps of d) inserting the spray tip into a body cavity or a wound cavity prior to expressing the first and second biocompatible components; and e) allowing the first biocompatible component and the second biocompatible component intermix in the body cavity or the wound cavity.

6. The method of claim 4, wherein said step of simultaneous spraying of the first and second biocompatible components is performed without mixing the first biocompatible component and the second biocompatible component in said spray tip.

7. The spray tip of claim 1, said spray tip further containing a plurality of channels in fluid communication with the first and second component distribution compartments and said plurality of first and said second exit orifices, and wherein said plurality of channels are positioned between said first and second component distribution compartments and said plurality of first and said plurality of second exit orifices.

8. The spray tip of claim 1, wherein the first biocompatible component comprises fibrinogen and the second biocompatible component comprises thrombin.

9. The spray tip of claim 1, wherein said plurality of first and said second exit orifices are positioned around the spray tip and are enabling spraying in direction orthogonal to a cylindrical surface of the spray tip.

10. The spray tip of claim 1, wherein said plurality of first exit orifices are in several axial arrays arranged along a length of the spray tip on a cylindrical surface of the spray tip, and said plurality of second exit orifices are in several axial arrays arranged along the length of the spray tip on the cylindrical surface of the spray tip, wherein said several axial arrays of the plurality if first exit orifices are interlaced or arranged one after another in alternating design with said several axial arrays of the plurality of second exit orifices.

11. The spray tip of claim 10, wherein said array of the plurality of first exit orifices is followed by said several axial array of the plurality of second exit orifices, followed again by said several axial of the plurality of first exit orifices.

* * * * *